United States Patent
Alekseenko et al.

(10) Patent No.: US 7,160,248 B2
(45) Date of Patent: *Jan. 9, 2007

(54) OPTICAL DEVICE FOR VIEWING OF CAVERNOUS AND/OR INACCESSIBLE SPACES

(75) Inventors: Sergei Alekseenko, Novosibirsk (RU);
Aleksey Evseev, Novosibirsk (RU);
Peter Belousov, Novosibirsk (RU);
Andrey Belousov, Novosibirsk (RU);
Lev Diamant, Korazim (IL); Yuri Dubnistchev, Novosibirsk (RU);
Dmitriy Markovich, Novosibirsk (RU);
Vladimir Meledin, Novosibirsk (RU);
Aleksander Staroha, Tomsk (RU)

(73) Assignee: Optiscope Technologies Ltd., Katzrin (IL)

(*) Notice: Subject to any disclaimer, the term of this patent is extended or adjusted under 35 U.S.C. 154(b) by 410 days.

This patent is subject to a terminal disclaimer.

(21) Appl. No.: 10/727,040

(22) Filed: Dec. 4, 2003

(65) Prior Publication Data

US 2004/0133071 A1 Jul. 8, 2004

Related U.S. Application Data

(63) Continuation-in-part of application No. 10/438,275, filed on May 15, 2003, now Pat. No. 7,018,330.

(51) Int. Cl.
A61B 1/00 (2006.01)

(52) U.S. Cl. ...................... 600/130; 600/160; 600/167; 359/434; 359/435

(58) Field of Classification Search ................ 600/129, 600/130, 160–168, 172, 176; 359/399–345
See application file for complete search history.

(56) References Cited

U.S. PATENT DOCUMENTS

| | | | |
|---|---|---|---|
| 4,964,710 A | 10/1990 | Leiner | |
| 5,188,092 A | 2/1993 | White | |
| 5,359,685 A | 10/1994 | Waynant et al. | |
| 5,396,366 A | 3/1995 | Brown et al. | |
| 5,423,312 A | 6/1995 | Siegmund et al. | |
| 5,782,825 A | 7/1998 | Anderson | |
| 5,841,578 A | 11/1998 | Hoogland | |
| 5,891,015 A | 4/1999 | Strähle | |
| 5,892,630 A | 4/1999 | Broome | |
| 6,398,724 B1 | 6/2002 | May et al. | |
| 6,730,019 B1* | 5/2004 | Irion | 600/178 |

* cited by examiner

*Primary Examiner*—Linda C. M. Dvorak
*Assistant Examiner*—Matthew J. Kasztejna
(74) *Attorney, Agent, or Firm*—Nath & Associates PLLC; Gregory B. Kang; Teresa M. Arroyo (57) ABSTRACT

An optical device for viewing an object at a range of working distances. The device comprises a slender tube of a certain length and having a distal end and a proximal end. The device further comprises an imaging system disposed at the distal end and having a wide viewing angle. The device also comprises a telescopic system associated with the proximal end and having a narrow viewing angle. The imaging system is designed to form an image of the object at an image plane located on the device's optical axis and within the tube closer to the distal end than to the proximal end. The telescopic system is designed to enable viewing of the image of the object. The device is especially adapted to function as an endoscope in medical applications and may be disposable.

26 Claims, 4 Drawing Sheets

OPTICAL DEVICE FOR VIEWING OF CAVERNOUS AND/OR INACCESSIBLE SPACES

This application is a continuation-in-part application of U.S. patent application Ser. No. 10/438,275, filed May 15, 2003 now U.S. Pat. No. 7,018,330, the contents of which are incorporated herein by reference in its entirety.

FIELD OF THE INVENTION

This invention relates to optical instruments adapted for viewing of cavernous and/or inaccessible spaces and which may be employed to view objects such as internal body organs and cavities thereof, as well as particular objects located in such organs, e.g. a tumor or a cyst. These optical instruments include endoscopes, otoscopes, laparoscopes, arthroscopes, bronchoscopes, laringoscopes, cystoscopes and other similar rigid endoscopic medical examination devices. Such optical instruments are not limited to medical use, however, and may be found in any of a variety of fields in which inspection as described above may be applicable, e.g. in mechanical applications, such as in the form of a borescope. More particularly, the invention relates to such optical instruments that are further designed to be disposable.

BACKGROUND OF THE INVENTION

Various optical instruments, which are designed to enable viewing of areas not easily accessible or directly available for inspection, are known in the art. In medical applications, for example, a plurality of optical instruments, such as endoscopes, arthroscopes, bronchoscopes, and the like, are used for examining the interior of body cavities ranging from ear canals to joints and lungs. Access to such cavities by these instruments is typically achieved via a natural body conduit constituting or leading to the cavity. In some cases, however, it is known to make a small surgical incision by which the instrument may gain access to the cavity.

Rigid and flexible endoscopes are known in the art. Unlike their rigid counterparts, flexible endoscopes allow access to considerably cavernous and distant areas of the body, such as the intestinal tract. However, when compared with rigid endoscopes, flexible endoscopes provide reduced image quality, are relatively expensive, and are not suitable for many applications. They are also normally not adapted to withstand sterilization by an autoclave.

Rigid endoscopes have advantages in the above respects, particularly as far as image quality is concerned. In general, a rigid endoscope comprises an elongated tube having a distal end for insertion into a body cavity, a proximal end with an eyepiece, and a plurality of lenses located inside the tube and along its length for forming an image of the body cavity, and/or objects located therein, and transferring the image to a viewing component, by which it may be viewed e.g. by a physician. Typically, the interior surface of the tube is black coated in order to prevent undesirable residual light reflections therein.

U.S. Pat. No. 5,891,015 discloses an endoscope comprising a rigid tube having a distal end, a proximal end with a viewing component including an image-sensitive surface, and an imaging system therebetween, which fully occupies the tube's interior and includes a single aspherical planar-concave front lens, a single aspherical inner lens, and two glass rods. The imaging system serves to form an image of the object and to subsequently relay it to the image-sensitive surface, which reads the image and enables it to be displayed for viewing.

U.S. Pat. No. 6,398,724 discloses an endoscope including a sealed insertion tube with a distal end and a proximal end, which is associated with a focusing assembly having optical components and being mounted in an endoscope housing to which the tube is detachably attachable. The insertion tube comprises optical elements located therein along its length and adapted to form an image of the object inside the focusing assembly, wherefrom the image is transferred by the optical components to an image plane coinciding with the image-sensitive surface of a CCD sensor. The image of the object may be focused by moving the CCD sensor so as to adjust the distance between the image-sensitive surface and the stationary image. The detachable insertion tube is autoclavable, and may therefore be sterilized alone, thereby eliminating the need to sterilize the entire endoscope, especially components thereof, such as the focusing assembly and the CCD sensor, whose adequate sterilization is considerably more complex and costly.

It is crucial for reuseable medical instruments to be sterilized before their reuse, and such sterilization is performed by various methods, such as by autoclaving. However, the delicate and complicated construction of reuseable endoscopes makes their absolute sterilization difficult to achieve.

Accordingly, a need in the art has developed for a disposable endoscope, which on the one hand, provides high quality imaging, while on the other, may be produced from relatively inexpensive components and manufactured sufficiently inexpensively as to be cost-effective for disposal after single-patient use.

Attempts to design disposable endoscopes are known and disclosures thereof include, for example, U.S. Pat. No. 4,964,710, U.S. Pat. No. 5,188,092, U.S. Pat. No. 5,892,630 and U.S. Pat. No. 5,423,312. U.S. Pat. No. 5,423,312 discloses a rigid endoscope with a disposable shaft comprising a rigid tube and a handle at a proximal end of the tube from which it may be disconnected. The rigid tube is occupied with a high refractive index rod having zero focusing power and relatively simple lenses incorporated at distal and proximal ends of the rod for image formation so as to cover a wide object field and to relay the image to a video camera. Illumination light conducting means in form of fibers, clad rods or aluminum coated transparent light conducting tube are suggested.

SUMMARY OF THE INVENTION

The present invention suggests an optical device for viewing an object at a range of working distances, the device having an optical axis and comprising a slender tube of a certain length and having a distal end and a proximal end, an imaging system disposed at said distal end and having a wide viewing angle, and a telescopic system associated with said proximal end and having a narrow viewing angle, the imaging system being designed to form an image of said object at an image plane located along said axis and within said tube closer to the distal end than to the proximal end, the telescopic system being designed to enable viewing of said image of the object.

Being associated with the proximal end of the slender tube the telescopic system of the optical device in accordance with the present invention is spaced from the imaging system and its image plane by a substantial part of the length of the slender tube which length is chosen depending on the intended application for which the device is designed. However, for any chosen length, the viewing angle of the telescopic system is always so narrow as to span no more than the slender tube's width at the location of the image plane. In this way, the telescopic system enables viewing of the image of the object without a need for intermediating image-forming optical components, such as a plurality of relay lenses within the tube to transfer the image to the image sensor (human eye, CCD camera, etc.) positioned at the proximal end of the device.

The wide viewing angle of the imaging system of the optical device according to the present invention may be as in conventional optical devices of the kind to which the present invention refers. Preferably, however, this viewing angle is so wide and, consequently, the imaging system possesses such a short focal length that the location of its image plane lies within the depth of field of the telescopic system over the entire range of working distances. Thus, the telescoping system may be fixed in a predetermined disposition, enabling the optical device to provide a clear view of the image of any object located within the working range, without requiring adjustment of the telescopic system.

To achieve the simplest and most inexpensive design possible for the optical device in accordance with the present invention, the imaging system possesses a minimum number of elements necessary to provide its wide viewing angle, with all of these elements being concentrated at the distal end of the tube. To this end, the imaging system preferably includes a single element in the form of a whole ball (i.e. a sphere) lens, which may have certain sections removed therefrom, e.g. an outer cylindrical portion of the sphere cut therefrom to yield a drum-like shape. The use of a ball lens is preferred not merely because such a lens possesses the shortest focal length possible for a single element, but also since it provides an added advantage of producing relatively little chromatic aberration and causing a negligible amount of distortions such as astigmatism and coma. Furthermore, geometric distortions produced by the ball lens may be easily calculated and may therefore also be easily corrected either by image processing techniques or optically, such as by incorporation of corrective optics. Such corrective optics preferably consists of a single corrective optical element adapted to reduce the distortions of the imaging system. The corrective optical element may be in any suitable form, such as that of a plano-convex lens, capable of achieving this end.

The imaging system of the optical device according to the present invention may alternatively contain an aspherical, wide viewing angle member having many of the desirable features of the ball lens but producing considerably less distortion, preferably to the extent that a corrective optical element would be unnecessary.

The imaging system may further include illumination light guide surrounding the circumference of the tube, which may be in any form known in the art, e.g. in the form of fiber optic strands or of an annular cylinder, extending along the tube.

Viewing of the image of the object obtained in an image plane of the telescopic system may be achieved directly with the human eye using the eyepiece of the telescope or indirectly therewith, such as via means for relaying the image to an image-sensitive device such as a video image sensor, photographic film, and the like, after which it may be displayed, e.g. on video screen.

One of the most essential applications of the optical device of the present invention is its use as an endoscope, in which case the slender tube is preferably rigid and may have any dimensions adapted for the intended application of the endoscope so long as the tube's total length is considerably greater than its width, with at least half of the tube length being free of image forming optical elements, since, as mentioned above, components of the imaging system are concentrated at the distal end, and the telescopic system is associated with or positioned in the vicinity of the proximal end of the tube. For example, for an imaging system including a ball lens, as mentioned above, having a diameter d, the entire imaging system is typically spread within the tube over a single continuous length of but about 2–3 times the diameter d, while the tube's total length spans about 10–100 times the diameter d.

The optical device of the present invention may further comprise transparent optical medium in the slender tube, filling the space between the imaging system and the telescoping system and/or the interior of the telescopic system. This medium may be in the form of one or more rods made of optical quality transparent material having refraction index exceeding 1. At least one of the rods may have one or both ends shaped so as to provide the rod with image focusing optical properties and/or with mechanical positioning means.

The present invention affords a simple design of an endoscope in comparison to many of those known in the art as it can operate with but a few optical elements, most of which are positioned at one of two locations i.e. near the distal end of the slender tube as part of the imaging system or near the proximal end as part of the telescopic system. Thus, the simple design of the endoscope of the present invention affords the device a number of considerable advantages including the device's relatively low sensitivity to bending forces and other mechanical loads that may be applied thereto during handling, when compared with relatively complicated endoscopic designs known in the art having many lenses and/or other optical elements, which have a tendency to render the endoscope optically inoperable even after slight bending, and often become damaged. Furthermore, the endoscope of the present invention is easily assembled, especially because its limited number of image-forming optical components is located at few and specific locations of the device, specifically near its extremities, or they may be simply "thrown in" into the slender tube one after the other in a predetermined order, as it can be done with the a.m. transparent rods.

In addition to the foregoing, the simple design of the present invention provides yet another advantage in the ability to thus produce a relatively inexpensive endoscope or other such device, which thereby also enables production of a completely disposable endoscope or of one having disposable parts, such as the rigid slender tube with its imaging system. Such an endoscope tube is, in fact, another aspect of the present invention.

The facility with which the endoscope or the endoscope tube of the present invention may be rendered sufficiently inexpensive to be disposable is a particularly beneficial feature in medical applications where instruments for introduction into the human body, for example, must often undergo sterilization.

Also, the simple design and assembly of the endoscope in accordance with the present invention enables its cost to be sufficiently minimized, particularly by choosing less expensive materials and methods for its manufacture, for example, that it may become economically feasible to dispose of the endoscope in its entirety after each use thereof. For example, the cost of the endoscope may be minimized by producing the imaging system, the telescopic system, the transparent rods, if any, the slender tube, as well as other parts of the endoscope body, from suitable plastic materials. In addition, the use of a ball lens in the imaging system, as mentioned above, for example, may be especially advantageous in this respect since, due to its simple geometry, the ball lens may be easily and inexpensively produced. Furthermore, due to its symmetry, the ball lens is easy to assemble, as its orientation is identical in any disposition.

When plastic transparent materials are used for manufacturing of the optical elements of the proposed invention, aspheric pressure molded plastic components may be used, thus further reducing the number of optical elements required and the resulting cost of the device.

Another example of a preferred manufacturing method includes production of the slender tube from a strip of metal sheeting which is blacked on one side by galvanic coating, paint, or other suitable material. The strip is then cold or hot drawn and welded to form the tube, with the blackened side constituting its inner surface to serve as a means, as known in the art, for preventing unwanted residual reflections of light from propagating through the tube and adversely affecting the image quality.

BRIEF DESCRIPTION OF THE DRAWINGS

In order to understand the invention and to see how it may be carried out in practice, different embodiments will now be described, by way of non-limiting example only, with reference to the accompanying drawings, in which.

DETAILED DESCRIPTION OF THE INVENTION

An endoscope 2 in accordance with the present invention is generally described below with reference to FIG. 1A. The endoscope 2 is adapted for viewing, by a viewer's eye E or an image-receiving viewing device e.g. a CCD camera (not shown), an object 3, such as an interior of a body organ or a tumor, within a predetermined range of working distances. The endoscope 2 comprises an imaging portion 2a and a viewing portion 2b arranged along a common optical axis O.

The imaging portion 2a includes a hollow rigid slender tube 4 with an imaging system 8 mounted therein. The slender tube 4 has a width w and a length L separating its distal end 5 and proximal end 6, the length L being considerably greater than the width w of the tube. The imaging system 8 is disposed within the tube 4 near its distal end 5 and is adapted to form an image of the object 3 on image plane 9 located adjacent to the imaging system 8. The imaging system 8 possesses such a wide viewing angle α, i.e. a short focal length, that the location of the image plane 9 varies only slightly in response to changes in the working distance. To provide the indicated wide viewing angle, the imaging system 8 comprises, for example, a single ball lens 12 of diameter d and a corrective optical element in the form of a plano-convex lens 13 adapted to reduce distortions produced by the ball lens 12. The imaging portion 2a further comprises a window 7 at the distal end 5 of the tube 4 in front of the ball lens 12.

The viewing portion 2b of the endoscope 2 includes a housing 11 to which the tube 4 is connected at its proximal end 6, and a telescopic system 10 accommodated within the housing 11. The telescopic system 10 comprises a first converging lens 20 and a second converging lens 22, thereby defining a Newtonian telescope arrangement. The telescopic system 10 possesses a narrow viewing angle β defined by the width w of the tube 4 and a distance between the image plane 9 and the first converging lens 20. Due to such a narrow viewing angle, and in view of the fact that the optical elements (i.e. the lenses 12 and 13) of the imaging system 8 are concentrated at the distal end 5 of the tube 4 and those (i.e. the lenses 20 and 22) of the telescopic system 10 are near the proximal end 6 of the tube 4, the majority of its length L is free of optical elements, especially between the image plane 9 and the telescopic system 10. Thus, for example, with the length L of the tube 4 being about 10–100 times the diameter d of the ball lens 12, and the imaging system 8 spanning a length of about 2–3 times the diameter d, about 70–98% of the length of the tube remains free of optical elements.

The telescopic system 10 has a predetermined depth of field and it is so spaced from the imaging system 8 as to ensure that the image plane 9, whose position varies only slightly with variation in the working distance due to the wide viewing angle of the imaging system, lies within the depth of field over the entire range of working distances. Thus, the telescoping system 10 may be fixed in a predetermined arrangement, while having its image plane between the lenses 20 and 22, thereby enabling the endoscope 2 to provide a clear view of the image of any object located within the range of working distances, thus eliminating a necessity for adjustment of the telescopic system 10.

The telescopic system 10 is designed to have magnification parameters such as to ensure that the image of the object 3 formed at the image plane 9 and viewed through the telescopic system, fully occupies the active part of the retina of the viewer's eye E or an image-sensitive surface of another image-receiving viewing device e.g. a CCD sensor. In this way, the telescopic system 10 enables viewing of the image of the object without a need for any intermediating components, such as a plurality of lenses within the tube, to transfer the image to the proximal end 6.

In operation, light rays reflected off the object 3 and entering the endoscope 2 through the window 7 along the optical axis O are converged by the ball lens 12 and the plano-convex lens 13 and an image (not shown) of the object 3 is formed at the image plane 9. The telescopic system 10 transfers the image from the image plane 9 via the image plane 21 to the viewer's eye E. As the working distance between the object 3 and the endoscope 2 changes, the location of the image plane 9 changes accordingly. Due to the very short focal length of the imaging assembly 8, however, the position of the image plane 9 is changed to such a slight extent that even for considerable changes in working distance, the telescoping system 10 will still enable clear viewing of the object's image. Therefore, the telescoping system 10 does not require adjustment despite variation in working distance.

The above-described operation of the endoscope according to the present invention has been modeled and tested by computerized simulations using commercially available ray-tracing programs and by theoretical calculations based thereon. In addition, test models of the endoscope have also been built, two examples of which are presented, for example, below.

| ENDOSCOPE PARAMETERS | Model 1 | Model 2 |
|---|---|---|
| 1. Length L of the tube 4 | 110 | 180 |
| 2. Range of working distances, mm | 3–∞ | 3–∞ |
| 3. Width w of the tube, mm | 3 | 3 |
| 4. Viewing angle of the imaging system (FOV), ° | 70 | 70 |
| 5. Focal length of the ball lens, mm | 2.2 | 2.2 |
| 6. Diameter d of the ball lens, mm | 3 | 3 |
| 7. Diameter of the corrective element, mm | 3 | 3 |
| 8. Magnification of the telescopic system | 5 | 7 |
| 9. Optical power of corrective element, diopters | 100 | 100 |
| 10. Optical power of telescopic system's first lens, diopters | 25 | 25 |
| 11. Optical power of telescopic system's second lens, diopters | 125 | 167 |
| 12. Depth of field of the telescopic system, mm | 1.4 | 1.4 |
| 13. Range of locations of the image plane (over the entire range of working distances), mm | 1.4 | 1.4 |

Figure 1A:
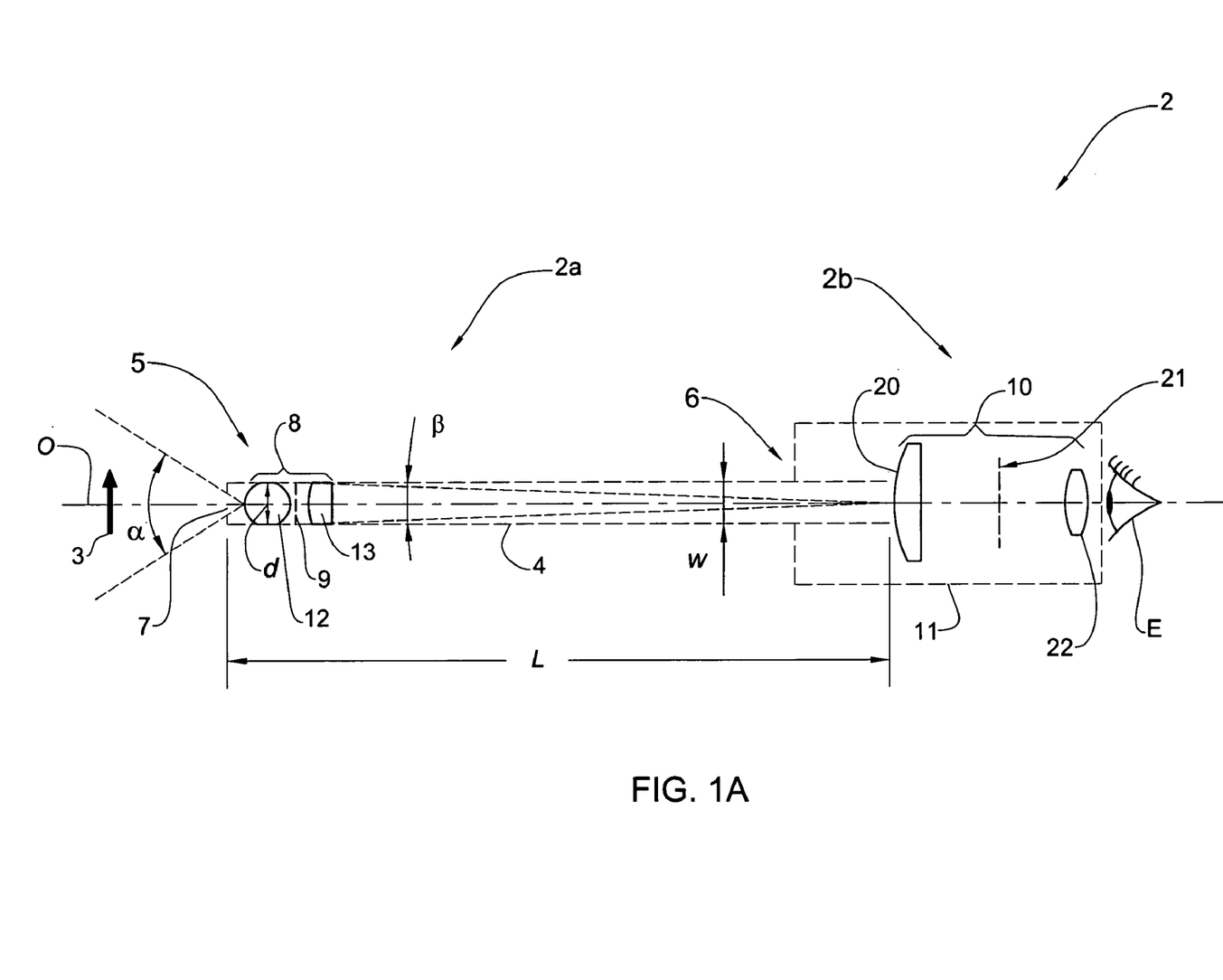
FIG. 1A is a schematic illustration of an optical set-up of an endoscope according to the present invention.
Figure 1B:
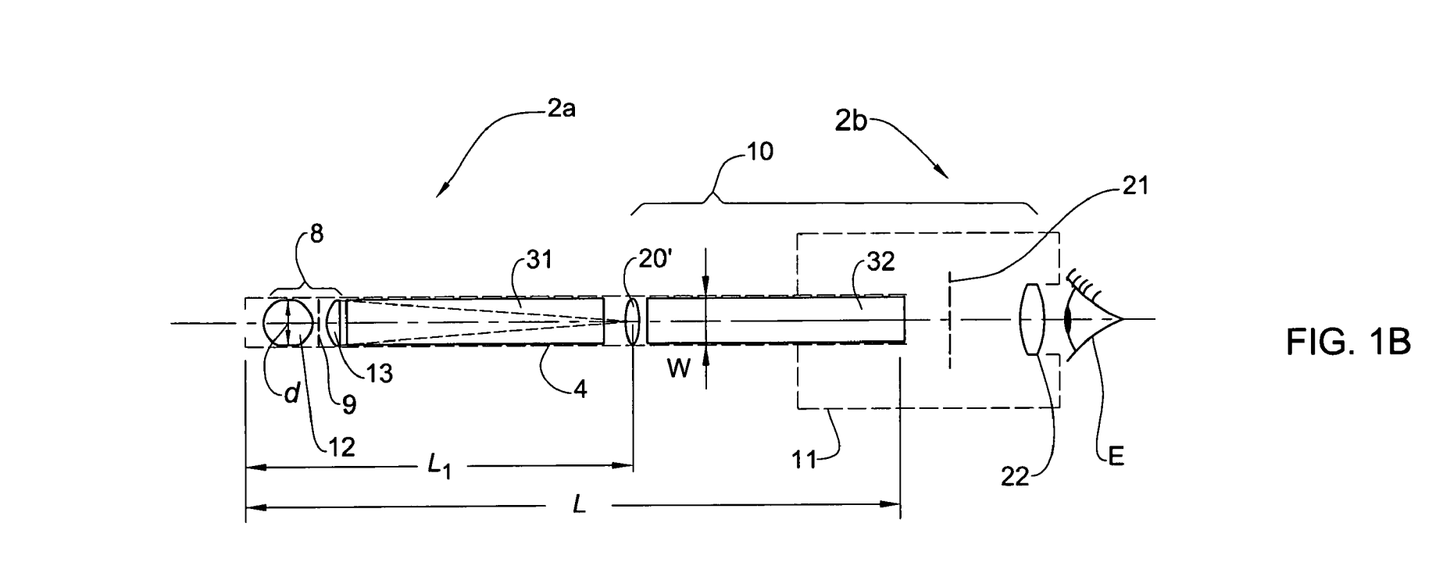
FIGS. 1B and 1C are schematic illustrations of variations of the optical set-up shown in FIG. 1A.

FIG. 1B illustrates an endoscope similar to that shown in FIG. 1A, where the telescopic system 10 has been modified by positioning its first converging lens 20' similar to lens 20 in FIG. 1A, inside the slender tube 4, and where transparent rods 31 and 32 having refractive index more than 1, have been introduced within the slender tube 4 on both sides of the lens 20'.

Figure 1C:
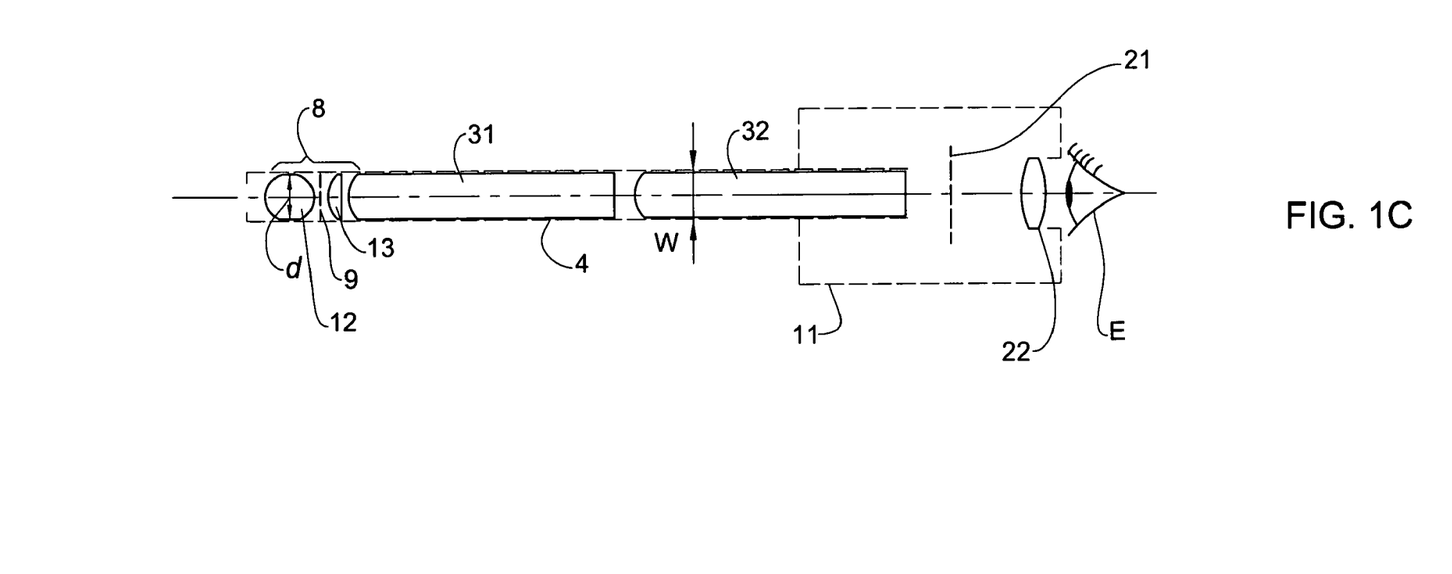

FIG. 1C illustrates an endoscope similar to that shown in FIG. 1B, where transparent rods 31' and 32' are formed with their distal ends formed as lenses. In the rod 31', the distal end is formed as a spherical or aspherical lens to perform a function of distortion correction in addition to or instead of the lens 13. In the rod 32, the distal end is formed as a lens replacing lens 20 in FIG. 1A or lens 20' in FIG. 1B. It may be preferable the rods are identical, to simplify the manufacturing and assembly of the endoscope. Clearly, only one of the rods may be formed with a lens at one of its ends. Also, each end of the rod(s) may be formed with a lens component made of material with refraction index that differs from the material of the rest of the rod, thus enabling chromatic correction if required. The outer part of the rod's end may be formed as a ring of a given length, thus providing proper spacing of the rod and simplifying the assembling process.

FIGS. 2 to 7 show three different embodiments of the endoscope of the present invention all based on the optical set-up and concept described above and shown in FIG. 1. In particular, each of the endoscopes includes an endoscope tube with the imaging system 8 at its distal end, and an endoscope housing receiving the proximal end of the tube and accommodating therein the telescopic system shown in FIG. 1. The endoscopes shown in FIGS. 2 to 7 all have illumination light guide means extending along the tubes from a location close to their proximal ends to their distal ends, for illuminating an object to be imaged. The illumination light guide means in the endoscopes include connectors mounted to the endoscope housing, which are connectable with a light guide of a light source (not shown).

Figure 2:
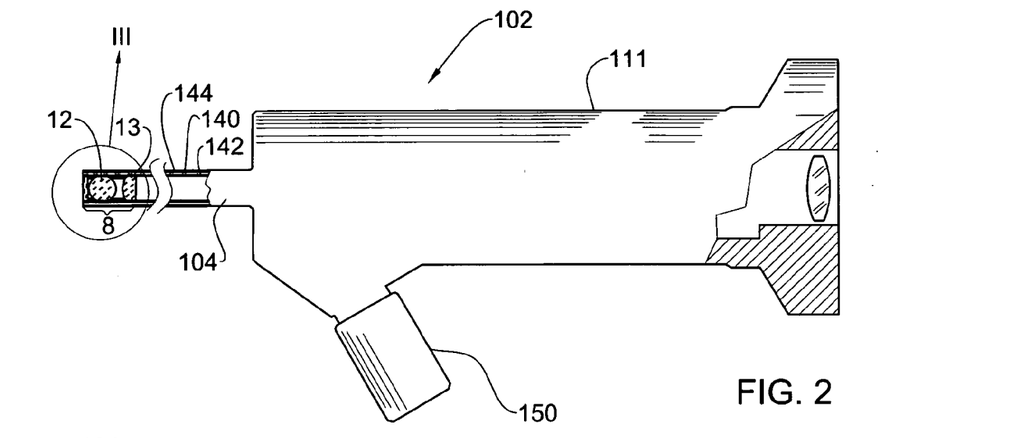
FIG. 2 is a schematic partial cross-sectional view of one embodiment of the endoscope illustrated in FIG. 1A.

FIG. 2 shows a reusable endoscope 102 including an endoscope tube 104 and housing 111 permanently coupled therewith. The tube 104 includes spaced apart internal sleeve 142 and external sleeve 144, and the endoscope comprises illumination light guide means in the form of fiber optics strands 140 which extend between the internal and external sleeves 142 and 144 of the tube 104 and through the housing 111 so as to enable communication with a light source via a connector 150, as known in the art.

Figure 3:
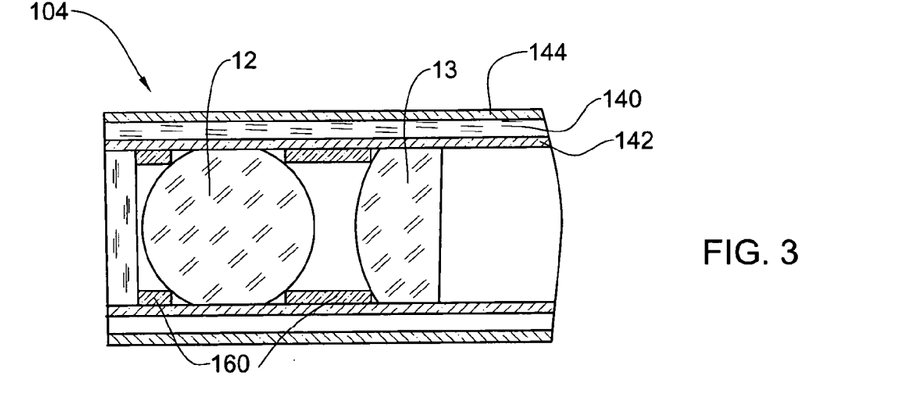
FIG. 3 is an enlarged cross-sectional view of a portion of the endoscope, designated as III in FIG. 2.

FIG. 3 shows an enlarged view of the distal end of the endoscope 102 shown in FIG. 2, illustrating the simple manner by which the lenses 12 and 13 are mounted in the internal sleeve 142 of the tube 104 together with spacers 160 therebetween, which serve to fix the lenses in a predetermined operational disposition.

Figure 4:
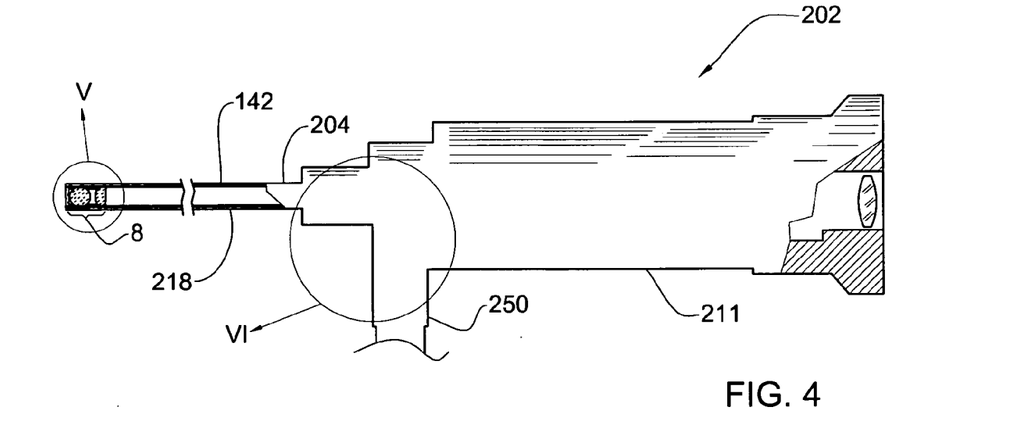
FIG. 4 is a schematic partial cross-sectional view of another embodiment of the endoscope illustrated in FIG. 1A.

FIG. 4 shows an endoscope 202 having a disposable endoscope tube 204, with its internal sleeve 142 containing the imaging system 8 as in the endoscope 102 described above and being devoid of an external sleeve. The endoscope 202 further includes a reusable endoscope housing 211, and the tube 204, detachably connected thereto. The illumination light guide means are in the form of an annular light guide cylinder 218 coaxially and contiguously adjoining the internal sleeve 142 to channel light from a light source via a connector 250 mounted in the housing 211.

Figure 5:
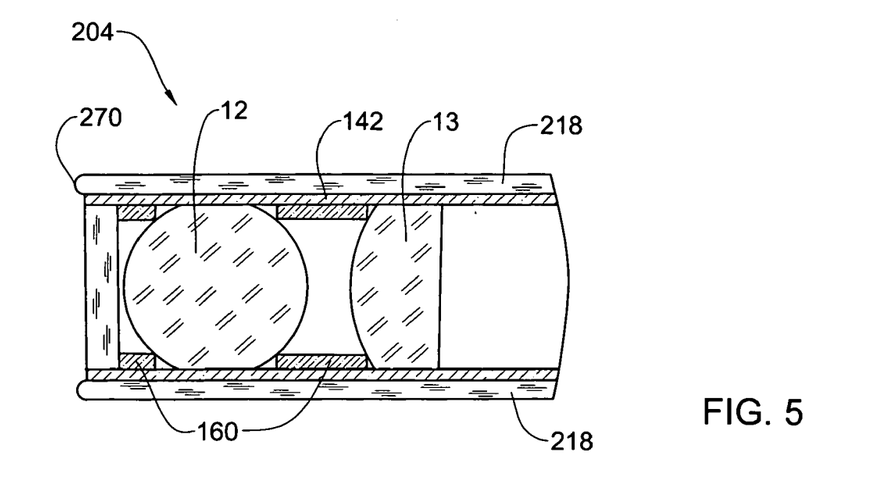
FIG. 5 is an enlarged cross-sectional view of a portion of the endoscopes, designated as V in FIG. 4.

FIG. 5 shows an enlarged view of the distal end of the endoscope 202 shown in FIG. 4, illustrating the light guide cylinder 218 extending along the internal sleeve 142 and having a bulged extremity 270 at the distal end of the tube 204.

The light guide cylinder 218 may be formed from a transparent material and have inner and outer surfaces coated with a material whose index of refraction is lower than that of the light guide material. The cylinder 218 is thus able to conduct light based on the principle of total internal reflection. Alternatively, the cylinder 218 may be coated on its outer and inner surfaces by a reflective coating, thereby also enabling it to efficiently channel light therethough. Various types of light guide cylinders are known in the art, and their means of connection to the connector 250 (shown in FIG. 4) may be learned therefrom, e.g. from U.S. Pat. No. 5,396,366 and U.S. Pat. No. 5,423,312.

The light guide cylinder 218 of the endoscope 202 according to the present invention is especially advantageous in comparison to a fiber optic arrangement, such as that described above with reference to FIGS. 2 and 3, in that it is considerably less expensive to produce and assemble. This allows the tube 204 to be made cost-effectively disposable, especially if the cylinder 218 as well as the imaging system 8 and the tube 204 itself are made from suitable low-cost materials and have easy-to-assemble design. In this way, the tube 204, including the imaging system 8 and the light guide cylinder 218, may be manufactured separately and detachably joined to the endoscope 202, so that it may be disjoined after use, disposed of, and replaced by another new such tube. Furthermore, the cylinder 218 is capable of transmitting more light than the arrangement of fiber optic strands 140 shown in FIGS. 2 and 3. The latter is due to the fact that spaces unavoidably existent between cylindrical fiber optic strands are, in the case of the cylinder 218, occupied by the material of the cylinder 218, which is also able to contribute to the amount of projected light.

To provide yet another advantage, during its manufacture, the extremity 270 of the light guide cylinder 218 is thermally processed to have the shape of a spherical bulge so as to enable light to be distributed therefrom at a relatively wide angle. Similarly, the extremity of the cylinder 218 in the endoscope of the present invention may be made, by any known methods, to have a wide variety of other designs adapted to direct the light projected therefrom in a desired intensity distribution to suit the viewing angle of the imaging system.

Figure 6:
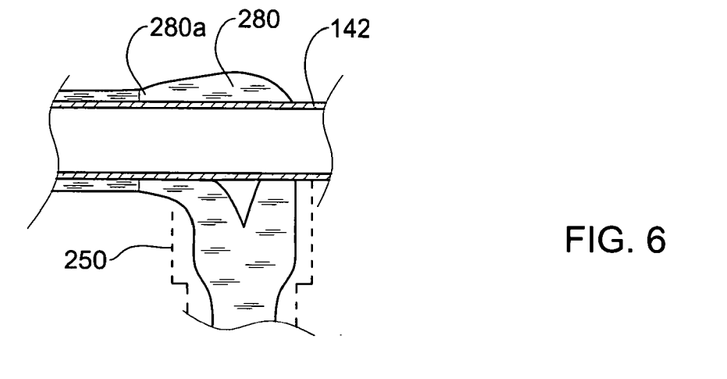
FIG. 6 is a schematic cross-sectional view of a portion of the endoscopes, designated as VI in FIGS. 5 and 7.

As shown in FIG. 6, the endoscope 202 (shown in FIGS. 4 and 5) has an L-shaped connecting light guide element 280, disposed on the internal sleeve 142 of the tube near its proximal end following the light guide cylinder 218 and extending into the connector 250. The element 280, which is annular in the region near its first end 280a but solid in the region adjacent its second end (not shown), is adapted to conduct light, at its second end, from the light guide means of the light source and channel it to the light guide cylinder 218, which it abuts at the first end 280a. The element 280 has a specific design directed to maximizing light transmission efficiency as its cross-sectional area at the first end 280a matches that of the cylinder 218, while tapering within the connector 250 near second end to match that of the light guide means of the light source. In this way, the element 280 serves to enable light to be conducted from the light source to the cylinder 218 with minimal loss of light therebetween.

Figure 7:
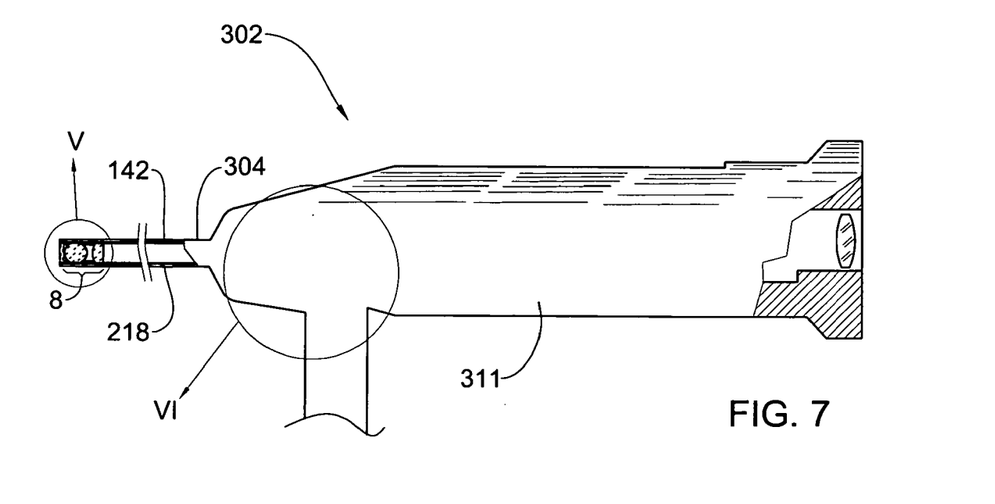
FIG. 7 is a schematic partial cross-sectional view of yet another embodiment of the endoscope illustrated in FIG. 1A.

FIG. 7 shows the endoscope 302, which is similar to the endoscope 202 of FIGS. 4–6 in the design of its tube 304, its light guide cylinder 218, and its light guide element 280, and differing only in that it is designed to be disposed of in its entirety following each use, i.e. its housing 311 with its telescopic system (shown in FIG. 1) accommodated therein is also disposable. The tube 304 may be integral or detachably connectable to the housing 311.

It should be understood that the above-described endoscopes are only examples of an optical device in accordance with the present invention and that the scope of the present invention fully encompasses other embodiments and applications that may become obvious to those skilled in the art. Thus, the optical device may be directed to enable viewing of any areas not easily accessible or directly available for inspection. As the device is particularly useful in a wide variety of medical fields where inspecting the confines of cavernous regions of a patient may be desired, the optical device may not only be used as an endoscope, but may be a part of any similar instrument including an otoscope, laparoscope, arthroscope, bronchoscope, laringoscope, cystoscope or other such endoscopic medical examination device, mutatis mutandis. Furthermore, while the present description focuses on the embodiment of the optical device of the present invention as an endoscope and the like, it should be noted that the device is not limited to medical use and may be employed in any of a variety of fields in which inspection as described above may be applicable, e.g. in mechanical applications such as in the form of a borescope, mutatis mutandis. In fact, the endoscopes shown in FIGS. 2–7 may also be used as borescopes.

In addition, the optical device described above may have additional components such as, for example, various light-deflecting elements (e.g. prisms), as known in the art, which, along with all other components of the imaging system, can be positioned at the distal end to enable viewing of objects distanced from the optical axis. For this purpose, the ball lens may have portions cut therefrom, as mentioned above, to give it a front frusto-conical shape so as to free up space to accommodate such elements.

Also, the endoscope may comprise a front window heating mechanism adapted to prevent vapor from condensing on the window's surface. The endoscopes' connectors 150 and 250 to the light source may also be positioned at other locations, e.g. at the far end of the housing opposite the distal end of the tube so as to be a hindrance during medical examinations and the like.

The invention claimed is:

1. An optical device for viewing an object comprising:
    an imaging system having a wide viewing angle and designed to form an image of said object at an image plane;
    a telescopic system having a narrow viewing angle and designed to enable viewing of said image of the object; and
    a slender tube having a distal end and a proximal end;
    said imaging system and said image plane being disposed at said distal end of the slender tube, and at least one lens of the telescopic system being disposed between said imaging system and said proximal end of the slender tube;
    said slender tube further comprising:
        transparent optical media having a refraction index greater than 1, substantially filling a space between said imaging system and said lens and/or between said lens and the proximal end of the slender tube.

2. An optical device according to claim 1, wherein said image plane is disposed distally to the optical media.

3. An optical device according to claim 1, wherein said transparent media is designed in the form of at least one transparent rod.

4. An optical device according to claim 3, wherein said transparent rod has a distal end formed as a lens.

5. An optical device according to claim 4, wherein said distal end of the transparent rod is designed to perform the function of said lens of said telescopic system disposed between said imaging system and said proximal end of the slender tube.

6. An optical device according to claim 1, herein said viewing angle of the imaging system is so wide and, consequently, its focal length is so short that said location of the image plane lies within the depth of field of the telescopic system over the entire range of working distances of the optical device.

7. An optical device according to claim 1, wherein the device is designed to be completely disposable.

8. An optical device according to claim 1, further comprising:
    a reusable section including at least a part of said telescopic system; and
    a disposable section in the form of said tube detachably mountable to said reusable section.

9. An optical device according to claim 1, wherein the device is an endoscope.

10. An optical device according to claim 1, wherein the device is a borescope.

11. An optical device according to claim 1, further including an illumination light guide designed to coaxially and contiguously adjoin said slender tube.

12. An optical device according to claim 11, wherein said light guide is composed of fiber optic strands.

13. An optical device according to claim 11, wherein said light guide is an annular cylinder.

14. An optical device according to claim 13, wherein said annular cylinder has an extremity processed to have a design adapted to direct the light projected therefrom in a desired intensity distribution suited to the viewing angle of the imaging system.

15. An optical device according to claim 14, further including a light guide element adapted to conduct light from a light source to the cylinder, the element being designed to match the cylinder at one end and to match the light source at the other end so as to reduce loss of light.

16. An optical device according to claim 1, further including one or more LEDs connected or connectable to an external power supply source or an internal battery.

17. An optical device according to claim 16, wherein said LEDs are placed at the distal end of the endoscope.

18. An optical device according to claim 16, wherein said LEDs are placed at the proximal end of the endoscope, in particular, at the end of its viewing portion.

19. An optical device according to claim 3, wherein the telescopic system comprises:
   a first converging lens and a second converging lens;
   said transparent media being in the form of two transparent rods; and
   said first converging lens being disposed between said two rods.

20. An optical device according to claim 1, further comprising:
   a housing, said proximal end of the slender tube being mounted within said housing so that a part of said telescopic system is disposed within said housing.

21. A slender tube for use in an optical device for viewing an object, the optical device comprising:
   a housing;
   an imaging system having a wide viewing angle and designed to form an image of said object at an image plane;
   a telescopic system having a narrow viewing angle and designed to enable viewing of said image of the object;
   said slender tube having a distal and a proximal end mountable within said housing so that a part of said telescopic system is disposed within said housing;
   the slender tube comprising:
      said imaging system located, together with said image plane, at the said distal end;
      a lens constituting a part of said telescopic system and disposed between said imaging system and said proximal end of the slender tube; and
      a transparent optical media having a refraction index greater than 1, substantially filling a space between said imaging system and said lens and/or between said lens and the proximal end of the slender tube.

22. An optical device according to claim 21, wherein said image plane is disposed distally to the optical media.

23. An optical device according to claim 21, wherein said transparent media is designed in the form of at least one transparent rod.

24. An optical device according to claim 23, wherein said transparent rod has a distal end formed as a lens.

25. An optical device according to claim 23, wherein said distal end of the transparent rod is designed to perform the function of said lens of said telescopic system disposed between said imaging system and said proximal end of the slender tube.

26. An optical device according to claim 21, wherein the telescopic system comprises:
   a first converging lens and a second converging lens;
   the transparent media being in the form of two transparent rods; and
   said first converging lens being disposed between said two rods.

* * * * *

UNITED STATES PATENT AND TRADEMARK OFFICE
CERTIFICATE OF CORRECTION

| | |
|---|---|
| PATENT NO. | : 7,160,248 B1 |
| APPLICATION NO. | : 09/727040 |
| DATED | : January 9, 2007 |
| INVENTOR(S) | : Alekseenko et al. |

It is certified that error appears in the above-identified patent and that said Letters Patent is hereby corrected as shown below:

TITLE PAGE, Please insert:
Item (60) Provisional application No. 60/385,888, filed on June 6, 2002

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,160,248 B2 |
| APPLICATION NO. | : 10/727040 |
| DATED | : January 9, 2007 |
| INVENTOR(S) | : Alekseenko et al. |

It is certified that error appears in the above-identified patent and that said Letters Patent is hereby corrected as shown below:

TITLE Page, Please insert:
(60)   Provisional application No. 60/385,888, filed on June 6, 2002

Signed and Sealed this

Twenty-ninth Day of May, 2007

JON W. DUDAS
*Director of the United States Patent and Trademark Office*